(12) United States Patent
Signorino et al.

(10) Patent No.: US 12,007,145 B2
(45) Date of Patent: Jun. 11, 2024

(54) APPARATUS FOR CLEANING A FLUID, IN PARTICULAR AIR

(71) Applicant: emz-Hanauer GmbH & Co. KGaA, Nabburg (DE)

(72) Inventors: Manfredi Signorino, Wackersdorf (DE); Martin Brabec, Nabburg (DE); Thomas Hanauer, Nabburg (DE)

(73) Assignee: EMZ-HANAUER GMBH & CO. KGAA, Nabburg (DE)

( * ) Notice: Subject to any disclaimer, the term of this patent is extended or adjusted under 35 U.S.C. 154(b) by 352 days.

(21) Appl. No.: 17/469,367

(22) Filed: Sep. 8, 2021

(65) Prior Publication Data
US 2022/0074614 A1   Mar. 10, 2022

(30) Foreign Application Priority Data
Sep. 10, 2020   (DE) .......................... 102020123644.1

(51) Int. Cl.
  *A61L 9/20*   (2006.01)
  *F24F 8/22*   (2021.01)
(52) U.S. Cl.
  CPC ............... *F24F 8/22* (2021.01); *A61L 9/205* (2013.01); *A61L 2209/111* (2013.01); *A61L 2209/16* (2013.01)
(58) Field of Classification Search
  CPC ....................................................... A61L 9/205
  See application file for complete search history.

(56) References Cited

U.S. PATENT DOCUMENTS

| | | | | |
|---|---|---|---|---|
| 6,656,424 | B1 * | 12/2003 | Deal | A61L 2/28 250/455.11 |
| 10,684,027 | B2 | 6/2020 | Goswami et al. | |
| 2019/0049129 | A1 * | 2/2019 | Huang | A61L 9/205 |
| 2019/0120508 | A1 * | 4/2019 | Goswami | F24F 8/80 |

FOREIGN PATENT DOCUMENTS

| | | |
|---|---|---|
| CN | 102318872 | 1/2012 |
| CN | 206113145 | 4/2017 |
| CN | 111397156 | 7/2020 |
| EP | 2711643 | 3/2014 |

OTHER PUBLICATIONS

Official Action (with English translation) for China Patent Application No. 202111059888.2, dated Dec. 9, 2022, 18 pages.
Official Action for Germany Patent Application No. 102020123644.1, dated Aug. 5, 2021, 11 pages.
Official Action for Germany patent Application No. 102020123644.1, dated Oct. 31, 2023, 10 pages.

\* cited by examiner

*Primary Examiner* — Donald R Spamer
(74) *Attorney, Agent, or Firm* — Sheridan Ross P.C.

(57) ABSTRACT

The invention relates to an apparatus for cleaning a fluid, in particular air, comprising a through-channel for the fluid, a radiation source device and a photocatalysis device, wherein the radiation source device emits electromagnetic radiation, wherein, in order to generate a photocatalytic reaction, the photocatalysis device can be exposed to at least some of the electromagnetic radiation, wherein a sensor device is provided to detect at least one change in radiation parameters of the electromagnetic radiation, wherein a control device is connected to the sensor device via signals, and wherein at least one control parameter of the radiation source device can be modified by means of the control device in the case of a deviation of the radiation parameter from a setpoint/threshold value or setpoint/threshold range.

13 Claims, 3 Drawing Sheets

APPARATUS FOR CLEANING A FLUID, IN PARTICULAR AIR

CROSS-REFERENCE TO RELATED APPLICATION

This application claims the benefit of German Patent Application No. 10 2020 123 644.1 filed Sep. 10, 2020, the entire contents of which are hereby incorporated herein by reference.

FIELD

The invention relates to an apparatus for cleaning a fluid, in particular air, comprising a through-channel for the fluid, a radiation source device and a photocatalysis device, the radiation source device emitting electromagnetic radiation, it being possible for the photocatalysis device to exposed to at least some of the electromagnetic radiation in order to generate a photocatalytic reaction.

BACKGROUND

Such a fluid is advantageously a mixture of gases, liquids, solids and microorganisms. This fluid is in particular air. Microorganisms present in the air, such as viruses, bacteria, yeasts and moulds, can endanger human health, contaminate raw materials and spoil food. Accordingly, it is advantageous to provide an apparatus which can clean a fluid, in particular air, and remove said microorganisms, such as viruses, bacteria, yeasts and moulds. Furthermore, the air can contain gases, liquids and solids which leave an unpleasant odour. This can occur, for example, in household appliances such as dishwashers and refrigerators.

A corresponding cleaning of the air can be carried out by a photocatalysis device, with the photocatalysis device being exposed to electromagnetic radiation in order to generate a photocatalysis reaction. The radiation source device usually has a limited service life. Furthermore, in the case of most radiation sources, the effectiveness, or the (power-intensity) output, decreases as the operating time increases. Accordingly, it is often necessary to replace the apparatus for cleaning a fluid or just the radiation source device.

SUMMARY

The problem addressed by the present invention consists in providing an apparatus for cleaning a fluid, in particular air, which overcomes the disadvantages mentioned at the outset. Furthermore, the problem addressed by the present invention is that of providing a method for controlling an apparatus for cleaning a fluid, in particular air, which overcomes the disadvantages mentioned at the outset. Finally, the problem addressed by the present invention is that of providing a household appliance comprising an apparatus for cleaning a fluid, in particular air, which overcomes the disadvantages mentioned at the outset.

This problem is solved by the subject matter of claims 1, 12 and 13. The dependent claims comprise preferred embodiments.

According to the invention, an apparatus for cleaning a fluid, in particular air, is provided, comprising a through-channel for the fluid, a radiation source device and a photocatalysis device, the radiation source device emitting electromagnetic radiation, it being possible for the photocatalysis device to be exposed to at least some of the electromagnetic radiation in order to generate a photocatalytic reaction, a sensor device being provided to detect at least one change in radiation parameters of the electromagnetic radiation, a control device being connected to the sensor device via signals, it being possible to modify at least one control parameter of the radiation source device by means of the control device in the case of a deviation of the radiation parameter from a setpoint/threshold value or setpoint/threshold value range.

The control device advantageously compares the data received from the sensor device with a setpoint/threshold value or a setpoint/threshold value range. In the case of a deviation from the setpoint/threshold value or the setpoint/threshold value range or that said value or range is fallen below or exceeded, the control device controls the radiation source device accordingly in order to modify the corresponding control parameter. The detection of change in a plurality of radiation parameters would also be conceivable.

According to a preferred embodiment, the photocatalysis device comprises at least one photocatalytic material. The photocatalysis device preferably comprises a photocatalysis surface which comprises at least one photocatalytic material. The photocatalytic material is preferably integrated in the photocatalysis surface. Preferably, at least the photocatalysis surface consists at least in part of at least one photocatalytic material. The photocatalysis surface of the photocatalysis device advantageously comprises portions made of a photocatalytic material. Preferably, at least the photocatalysis surface of the photocatalysis device consists entirely of a photocatalytic material. The photocatalysis surface is preferably exposed to the electromagnetic radiation from the radiation source device.

The photocatalytic material of the photocatalysis device is preferably a semiconductor. Semiconductors are usually described by what is referred to as the band model and comprise a conduction band and a valence band, which are energetically separated from one another by what is referred to as the band gap. The size of the band gap varies with the corresponding individual semiconductor material. The valence band and the conduction band are occupied by electrons according to the Fermi distribution. Accordingly, at absolute zero, the valence band is occupied and the conduction band is unoccupied. An incident photon can generate an electron-hole pair if the energy of the photon is greater than or equal to the energy difference of the band gap. As a result of the mobile electrons in the conduction band, a chemical or photocatalytic reaction advantageously takes place in the photocatalytic material in the form of a reduction of a particle of the air or fluid. Such a particle can preferably be a molecule, an ion or an atom. This reduction can already change the chemical properties of certain components such that they no longer cause an unpleasant odour or can be removed more easily, for example by washing off. Furthermore, the chemical or photocatalytic reaction can generate free radicals. Free radicals are molecules, ions, or atoms having an unpaired electron and are highly reactive. These free radicals can advantageously react with the undesirable microorganisms and gases in the air and kill them and convert them into other gases, respectively. The air is thus cleaned of unwanted microorganisms and unwanted gases which cause unpleasant odours.

According to a preferred embodiment, the photocatalytic material is titanium (IV) oxide, titanium dioxide, $TiO_2$. The radiation source device preferably emits electromagnetic radiation having a wavelength of less than 400 nm. The radiation source device advantageously emits UV radiation. The emitted electromagnetic radiation, preferably in the form of UV radiation, impinges on the photocatalysis device or the photocatalysis surface and causes the above-described photocatalytic reaction. In the case of an advantageous use of titanium dioxide, a generation of an electron-hole pair and the described chemical or photocatalytic reaction takes place in the case of irradiation with UV radiation. Titanium dioxide can preferably remove natural and artificial impurities in air and water by means of irradiation with UV radiation by the oxygen in the air being reduced and the impurities being oxidised (mineralised) into environmentally friendly end products. Furthermore, the surface of titanium dioxide can advantageously become superhydrophilic as a result of absorption of UV radiation. The radiation source device advantageously emits electromagnetic radiation having a wavelength in a range of from 380 nm to 315 nm. Such radiation is also referred to as so-called UV-A radiation. However, the use of UV-B radiation (315 nm-280 nm) and UV-C radiation (280 nm-100 nm) would also be conceivable. In the case of an advantageous use of UV-C radiation, this radiation would already have a corresponding effect on the fluid. The short-wave UV radiation in particular has a strong bactericidal effect. Said short-wave UV radiation is absorbed by the DNA of the microorganisms and destroys its structure there. In this way the living cells are inactivated. However, radiation sources for UV-C radiation are comparatively expensive.

According to a further advantageous embodiment, the radiation source device comprises at least one radiation source. The at least one radiation source is preferably a light-emitting diode LED. The at least one radiation source is preferably a UV LED.

According to a further advantageous embodiment, an efficiency ($\eta_{tot}$) of the apparatus for cleaning a fluid is a product comprising an optical or geometric efficiency ($\eta_{opt}$), an efficiency of the radiation source device ($\eta_{Rs}$) and an efficiency of the photocatalysis device ($\eta_{Pc}$):

$$\eta_{tot} = \eta_{Rs}(t) \cdot \eta_{opt} \cdot \eta_{Pc}$$

The optical or geometric efficiency describes the proportion of the emitted electromagnetic radiation that impinges on the photocatalysis surface and can thus cause the photocatalytic reaction. The efficiency of the photocatalysis device ($\eta_{Pc}$) describes the material-related circumstances which influence the absorption of electromagnetic radiation by the photocatalysis surface. For example, a portion of the electromagnetic radiation is reflected on the photocatalysis surface. This portion is therefore not absorbed and does not contribute to the formation of the photocatalytic reaction.

The efficiency of the radiation source device ($\eta_{Rs}$) comprises the radiant power or radiant flux which is emitted by the radiation source. In the case of most radiation sources, in particular in the case of the preferred UV LEDs, the radiant power decreases as the operating time increases. The service life of a UV LED is preferably the time at which the radiant power has dropped to approx. 50% of the initial value. The aging is preferably approximately linear. The service life depends on the relevant semiconductor material and the operating conditions, such as temperature and operating current. Usually, the aging of LEDs is primarily attributed to the enlargement of imperfections in the crystal due to thermal influences. Accordingly, the efficiency of the radiation source device ($\eta_{Rs}(t)$) is time-dependent. The radiation parameter is therefore preferably the radiant power of the radiation source device. The total radiant power ($P_{Tot}$) of the radiation source device is the product of the number (N) of radiation sources and the radiant power ($P_N$) of the individual radiation sources:

$$P_{Tot} = N \cdot P_N$$

An average value of the individual radiant powers ($P_N$) is approximately assumed in this case. The individual radiant power $P_N$ and the total radiant power ($P_{Tot}$) are dependent on the operating current (I(t)). The efficiency of the radiation source device ($\eta_{Rs}(t)$) is thus $$\eta_{Rs}(t) = \frac{P_{Tot}(I(t))}{P_{Tot}(I(t_0))}$$

The time ($t_0$) is in this case the starting time or the initial start-up of the apparatus.

Electromagnetic radiation having an optimal or maximum radiation parameter, preferably in the form of the optimal total radiant power ($P_{TotOPT}$), can be emitted by the radiation source device. A first number ($N_1$) of radiation sources can preferably be operated to emit the optimal radiation parameter. A first number ($N_1$) of radiation sources can advantageously be operated with a maximum operating current ($I_{max}$).

According to a further preferred embodiment, the radiation source device comprises a total number ($N_{tot}$) of radiation sources. The total number ($N_{tot}$) of radiation sources is preferably greater than or equal to 2. The total number ($N_{tot}$) of radiation sources in the radiation source device is preferably greater than the first number ($N_1$).

According to a further preferred embodiment, the at least one control parameter is an operating current ($I_O$). The operating current ($I_O$) is preferably smaller than the maximum operating current ($I_{max}$), at least in a first operating state. An operating number ($N_{tot}$) of radiation sources preferably corresponds to the total number ($N_{tot}$) of radiation sources. In this advantageous operating mode, a larger number of radiation sources is thus operated with a smaller operating current, as a result of which the optimal radiation parameter, preferably in the form of the optimal total radiant power ($P_{TotOPT}$), can be emitted by the radiation source device. In this case, it is advantageous that the operating current ($I_O$) of the operated radiation sources can be increased by means of the control device in the case of a deviation of the radiation parameter from a setpoint value range in the form of falling below a threshold value. The increase in the operating current ($I_O$) is dimensioned such that the optimal radiation parameter, preferably in the form of the optimal total radiant power ($P_{TotOPT}$), can be emitted by the radiation source device by means of the unchanged operating number ($N_O$) of radiation sources. This increase can preferably take place even more times in the form of further operating states, a deviation of the radiation parameter from a setpoint value range, in the form of falling below a threshold value, being detected in each further operating state. In a final operating state, the operating current ($I_O$) is advantageously equal to the maximum operating current ($I_{max}$). The advantageous apparatus can accordingly be operated much longer than an apparatus which uses a maximum operating current for a smaller number of radiation sources.

According to a further advantageous embodiment, the at least one control parameter is an operating number ($N_O$) of radiation sources. The operating number ($N_O$) of radiation sources is preferably smaller than the total number ($N_{tot}$) of radiation sources, at least in a first operating state. The operating number ($N_{tot}$) of radiation sources is preferably operated with the maximum operating current ($I_{max}$). In this case it is advantageous that the operating number ($N_O$) of radiation sources can be increased by means of the control device in the case of a deviation of the radiation parameter from a setpoint value range in the form of falling below a threshold value. The increase in the operating number ($N_O$) of radiation sources is dimensioned such that the optimal radiation parameter, preferably in the form of the optimal total radiant power ($P_{totOPT}$), can be emitted by the radiation source device with the unchanged operating current ($I_O$). This increase can preferably take place even more times in the form of further operating states, a deviation of the radiation parameter from a setpoint value range, in the form of falling below a threshold value, being detected in each further operating state. In a final operating state, the operating number ($N_O$) of radiation sources is advantageously equal to the total number ($N_{tot}$) of radiation sources. The advantageous apparatus can accordingly be operated much longer than an apparatus which uses a smaller number of radiation sources.

According to a further advantageous embodiment, two control parameters are provided in the form of the operating number ($N_O$) of radiation sources and the operating current ($I_O$). The operating number ($N_O$) of radiation sources is preferably smaller than the total number ($N_{tot}$) of radiation sources, at least in a first operating state. The operating current ($I_O$) is preferably smaller than the maximum operating current ($I_{max}$), at least in a first operating state. In this case, it is advantageous that the operating number ($N_O$) of radiation sources and the operating current ($I_O$) of the operated radiation sources can be increased by means of the control device in the case of a deviation of the radiation parameter from a setpoint value range in the form of falling below a threshold value. The increase in the operating number ($N_O$) and the operating current ($I_O$) of radiation sources is dimensioned such that the optimal radiation parameter can be emitted, preferably in the form of the optimal total radiant power ($P_{TotOPT}$), by the radiation source device. This increase can preferably take place even more times in the form of further operating states, a deviation of the radiation parameter from a setpoint value range, in the form of falling below a threshold value, being detected in each further operating state. In a final operating state, the operating number ($N_O$) of radiation sources is advantageously equal to the total number ($N_{tot}$) of radiation sources, and the operating current ($I_O$) is advantageously equal to the maximum operating current ($I_{max}$). The advantageous apparatus can accordingly be operated much longer than an apparatus which uses a smaller number of radiation sources.

It would also be conceivable that a first control parameter is increased by means of the control device in the case of a first deviation of the radiation parameter from a setpoint value range in the form of falling below a threshold value, and a second control parameter is increased in the case of a further deviation of the radiation parameter from a setpoint value range in the form of falling below a threshold value. The control parameters are preferably increased alternately in each further operating state. The operating number ($N_O$) of radiation sources could thus be increased in a first operating state, and the operating current ($I_O$) in a further operating state. The reverse sequence is also conceivable. In each operating state, the relevant increase in the control parameter is dimensioned such that the optimal radiation parameter can be emitted, preferably in the form of the optimal total radiant power ($P_{TotOPT}$), by the radiation source device.

According to a further advantageous embodiment, the at least one radiation source is arranged on a carrier device. The carrier device is advantageously plate-like. The carrier device is preferably designed as a circuit board or printed circuit board (PCB). The carrier device is preferably arranged substantially opposite the photocatalysis device. The through-channel for the fluid, in particular air, is advantageously provided between the carrier device and the photocatalysis device. As a result of an arrangement of this kind, an optimal irradiation of the photocatalysis surface by means of the electromagnetic radiation can take place. Furthermore, an optimal contact of the photocatalysis surface with the fluid can be ensured.

According to a further advantageous embodiment, the sensor device comprises at least one sensor. The electromagnetic radiation detected by the at least one sensor is preferably emitted directly by the radiation source device and/or reflected by the photocatalysis device. The at least one sensor is advantageously arranged on the carrier device. A sensor arranged in this way preferably detects at least some of the electromagnetic radiation reflected by the photocatalysis surface. Alternatively or cumulatively, the at least one sensor is arranged to the side of the radiation source device or to the side of the carrier device. The at least one laterally arranged sensor can advantageously be arranged on a separate carrier plate, preferably in the form of a printed circuit board. The at least one laterally arranged sensor preferably detects electromagnetic radiation which is emitted directly by the radiation source device and/or is reflected by the photocatalysis device.

A first detected value of the sensor device is preferably stored in a memory device. This first value is advantageously assigned to the optimal radiation parameter. It is also assumed that the radiation parameter changes analogously to the value measured by the sensor device. The setpoint/threshold value or setpoint/threshold value range can therefore preferably be determined on the basis of the first detected value. Any degenerating properties of the sensor device, which can distort the measurement result, are advantageously ignored.

The present problem addressed by the invention is also solved by a method for controlling an apparatus for cleaning a fluid, in particular air. The method can be equipped with all the features already described above in the context of the apparatus individually or in combination with each other and vice versa.

The method for controlling an apparatus for cleaning a fluid, in particular air, comprising a through-channel for the fluid, a radiation source device and a photocatalysis device, the radiation source device emitting electromagnetic radiation, it being possible for the photocatalysis device to be exposed to at least some of the electromagnetic radiation in order to generate a photocatalytic reaction, comprises the following method steps:

a) detecting at least one radiation parameter of the electromagnetic radiation by means of a sensor device;
b) comparing the detected sensor data with a setpoint value range by means of the control device;
c) modifying at least one control parameter of the radiation source device.

According to a preferred embodiment, the at least one control parameter is an operating current ($I_O$). The operating current ($I_O$) is preferably smaller than the maximum operating current ($I_{max}$), at least in a first operating state. An operating number ($N_O$) of radiation sources preferably corresponds to the total number ($N_{tot}$) of radiation sources. The operating current ($I_O$) of the operated radiation sources is preferably increased by means of the control device in the case of a deviation of the radiation parameter from a setpoint value range in the form of falling below a threshold value. The increase in the operating current ($I_O$) is dimensioned such that the optimal radiation parameter, preferably in the form of the optimal total radiant power ($P_{totOPT}$), can be emitted by the radiation source device by means of the unchanged operating number ($N_O$) of radiation sources. This increase can preferably take place even more times in the form of further operating states, a deviation of the radiation parameter from a setpoint value range, in the form of falling below a threshold value, being detected in each further operating state. In a final operating state, the operating current ($I_O$) is advantageously equal to the maximum operating current ($I_{max}$).

According to a further preferred embodiment, the at least one control parameter is an operating number ($N_O$) of radiation sources. The operating number ($N_O$) of radiation sources is preferably smaller than the total number ($N_{tot}$) of radiation sources, at least in a first operating state. The operating number ($N_O$) of radiation sources is preferably operated with the maximum operating current ($I_{max}$). The operating number ($N_O$) of radiation sources is advantageously increased by means of the control device in the case of a deviation of the radiation parameter from a setpoint value range in the form of falling below a threshold value. The increase in the operating number ($N_O$) of radiation sources is dimensioned such that the optimal radiation parameter, preferably in the form of the optimal total radiant power ($P_{TotOPT}$), can be emitted by the radiation source device with the unchanged operating current ($I_O$). This increase can preferably take place even more times in the form of further operating states, a deviation of the radiation parameter from a setpoint value range, in the form of falling below a threshold value, being detected in each further operating state. In a final operating state, the operating number ($N_O$) of radiation sources is advantageously equal to the total number ($N_{tot}$) of radiation sources.

According to a further preferred embodiment, two control parameters are provided in the form of the operating number ($N_O$) of radiation sources and the operating current ($I_O$). The operating number ($N_O$) of radiation sources is preferably smaller than the total number ($N_{tot}$) of radiation sources, at least in a first operating state. The operating current ($I_O$) is preferably smaller than the maximum operating current ($I_{max}$), at least in a first operating state. The operating number ($N_O$) of radiation sources and the operating current ($I_O$) of the operated radiation sources are advantageously increased by means of the control device in the case of a deviation of the radiation parameter from a setpoint value range in the form of falling below a threshold value. The increase in the operating number ($N_O$) and the operating current ($I_O$) of radiation sources is dimensioned such that the optimal radiation parameter can be emitted, preferably in the form of the optimal total radiant power ($P_{TotOPT}$), by the radiation source device. This increase can preferably take place even more times in the form of further operating states, a deviation of the radiation parameter from a setpoint value range, in the form of falling below a threshold value, being detected in each further operating state. In a final operating state, the operating number ($N_O$) of radiation sources is advantageously equal to the total number ($N_{tot}$) of radiation sources, and the operating current ($I_O$) is advantageously equal to the maximum operating current ($I_{max}$).

The present problem addressed by the invention is also solved by a household appliance, an air conditioner or an air conditioning system, comprising an apparatus for cleaning a fluid, in particular air. The household appliance, the air conditioner or the air conditioning system can in this case be equipped with all the features already described above in the context of the apparatus individually or in combination with each other and vice-versa. The apparatus can in this case be operated using a method for controlling an apparatus for cleaning a fluid, in particular air. Accordingly, the household appliance, the air conditioner or the air conditioning system can in this case be equipped with all of the features already described above in the context of the method for controlling an apparatus for cleaning a fluid, in particular air, individually or in combination with one another and vice versa.

Such a household appliance can advantageously be a dishwasher, a refrigerator, a washing machine or some other household appliance.

BRIEF DESCRIPTION OF THE DRAWINGS

Further advantages, aims and properties of the present invention will be explained with reference to the following description of the accompanying drawings. Similar components may have the same reference signs in the various embodiments.

In the drawings.

DETAILED DESCRIPTION

Figure 1:
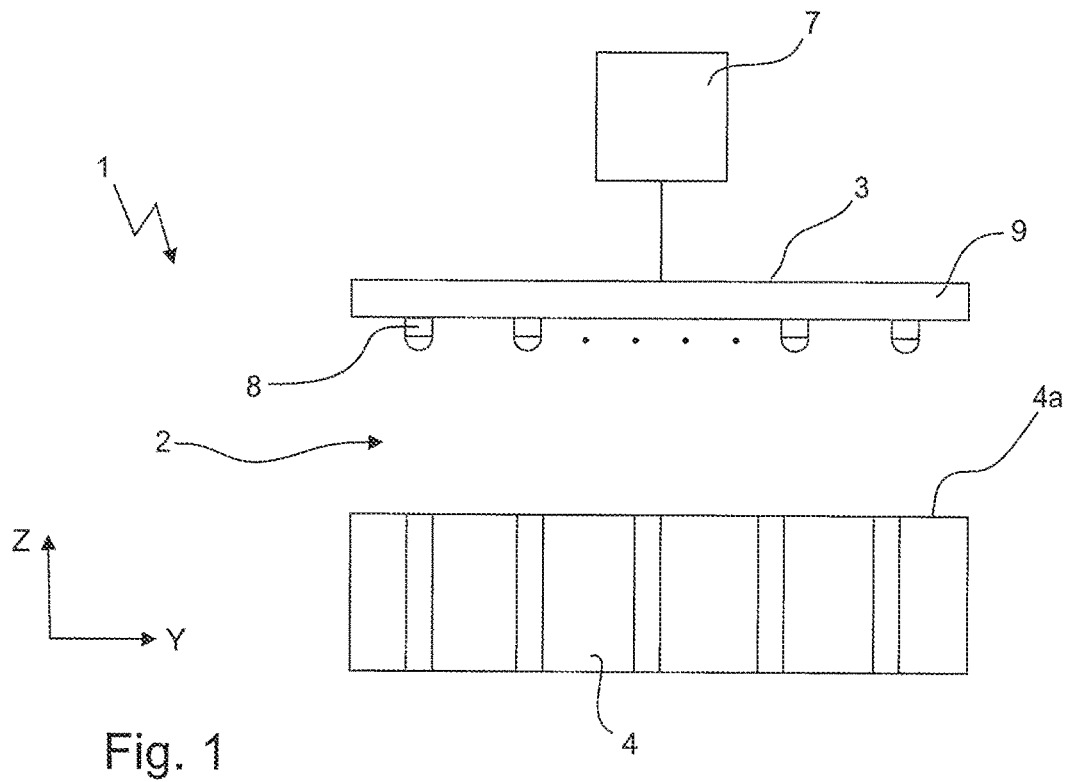
FIG. 1 shows an apparatus for cleaning a fluid according to an embodiment.

FIG. 1 to 4 show an apparatus 1 for cleaning a fluid, in particular air, comprising a through-channel 2 for the fluid, a radiation source device 3 and a photocatalysis device 4, the radiation source device 3 emitting electromagnetic radiation 5, it being possible for the photocatalysis device 4 to be exposed to at least some of the electromagnetic radiation 5 in order to generate a photocatalytic reaction, a sensor device 6 being provided to detect at least one change in radiation parameters of the electromagnetic radiation 5, a control device 7 being connected to the sensor device 6 via signals, and at least one control parameter of the radiation source device 3 being modifiable by means of the control device 7 in the case of a deviation of the radiation parameter from a setpoint/threshold value or setpoint/threshold value range.

In addition, FIG. 1 to 6 show a method for controlling an apparatus 1 for cleaning a fluid, in particular air, comprising a through-channel 2 for the fluid, a radiation source device 3 and a photocatalysis device 4, the radiation source device 3 emitting electromagnetic radiation 5, it being possible for the photocatalysis device 4 to be exposed to at least some of the electromagnetic radiation 5 in order to generate a photocatalytic reaction, the method comprising the following method steps:

a) detecting at least one radiation parameter of the electromagnetic radiation 5 by means of a sensor device 6;
b) comparing the detected sensor data with a setpoint value range by means of the control device 7;
c) modifying at least one control parameter of the radiation source device 3.

The apparatus 1 extends along a height axis Z, a width axis Y and a longitudinal axis X.

Figure 2:
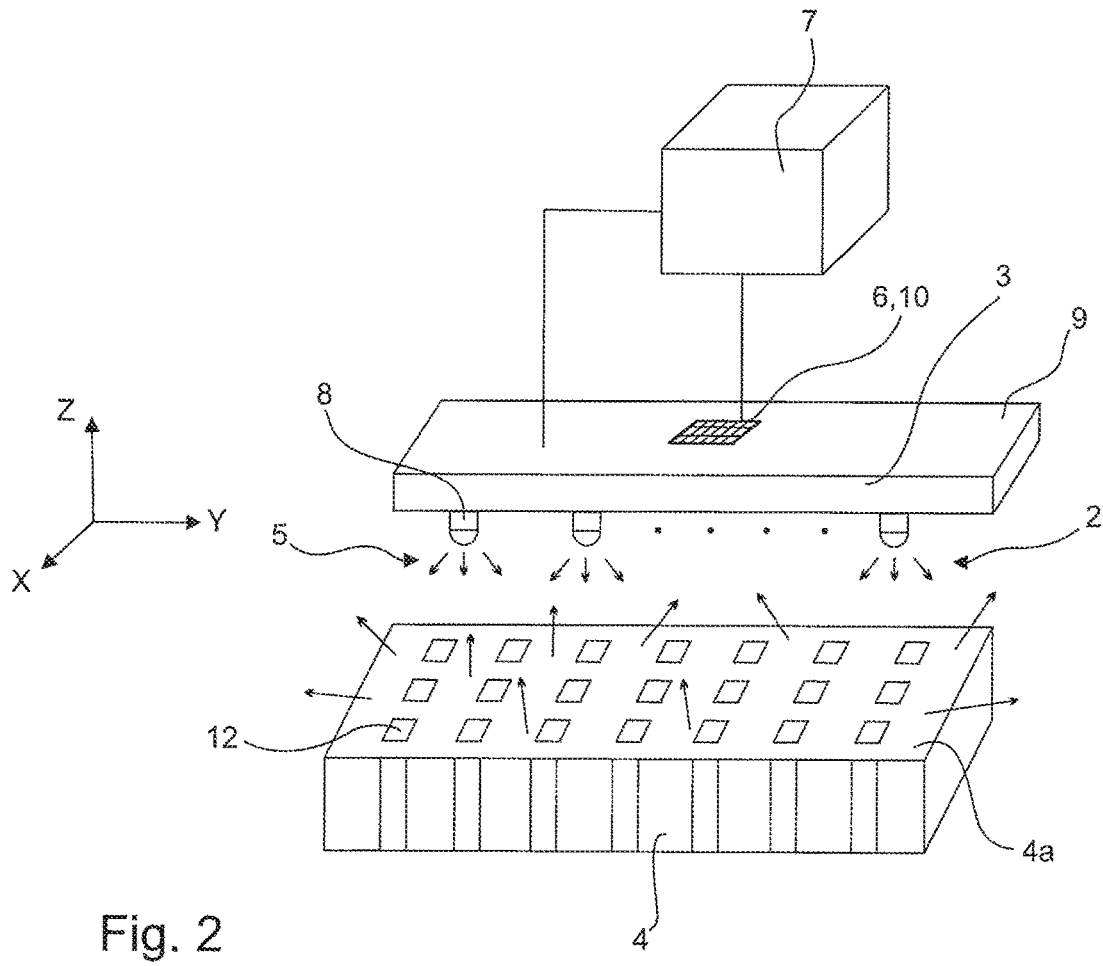
FIG. 2 shows an apparatus for cleaning a fluid according to an embodiment.
Figure 4:
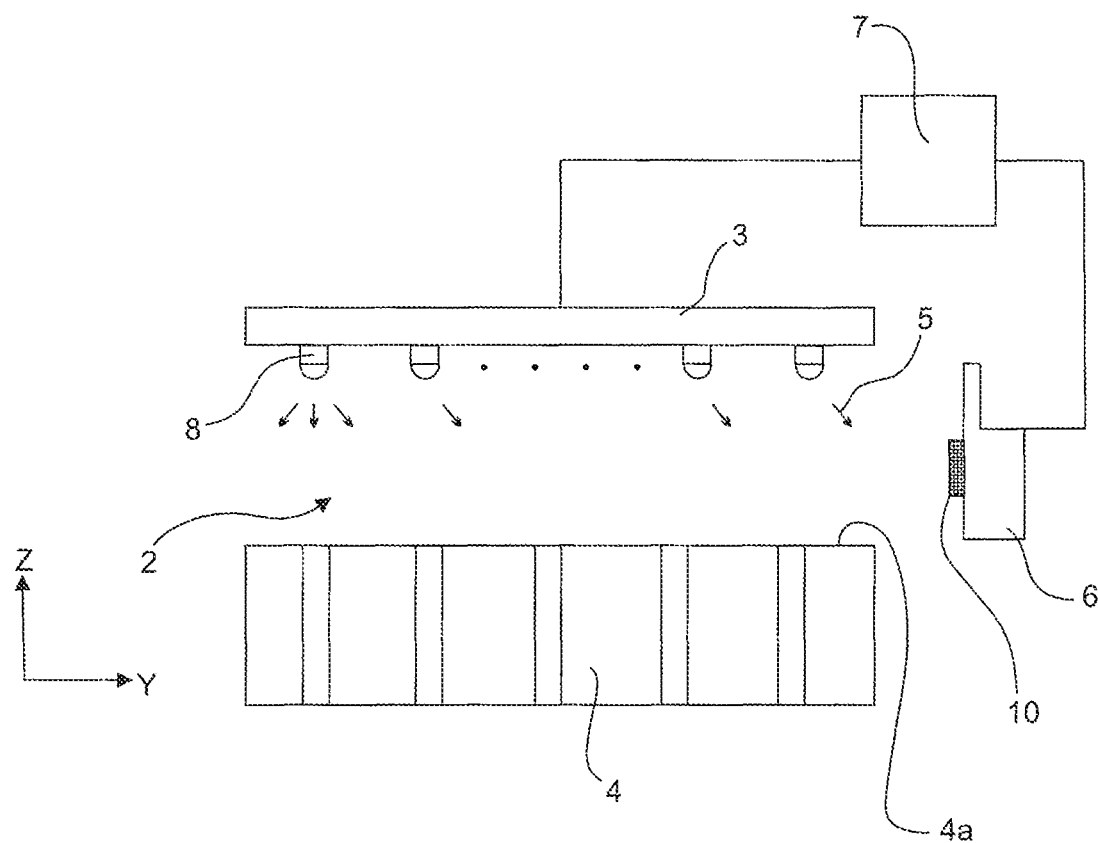
FIG. 4 shows an apparatus for cleaning a fluid according to an embodiment.

The radiation source device 3 comprises at least one radiation source 8, the at least one radiation source 8 being a light-emitting diode (LED). The radiation source device 3 comprises a large number of radiation sources 8, having a total number $N_{tot}$ of radiation sources 8. The radiation sources 8 or the carrier device 9 are/is opposite the photocatalysis device 4 and the through-channel 2 for the fluid is provided between the carrier device 9 and the photocatalysis device 4. The carrier device 9 extends in a plane which is spanned by the width axis Y and a longitudinal axis X. The photocatalysis device 4 comprises a photocatalysis surface 4a. This photocatalysis surface 4a also extends in a plane which is spanned by the width axis Y and a longitudinal axis X. The radiation source device 3, or the carrier device 9 having the radiation sources 8 is spaced apart from the photocatalysis device 3 or the photocatalysis surface 4a along the height axis Z. This is shown in FIGS. 1, 2 and 4.

Figure 3:
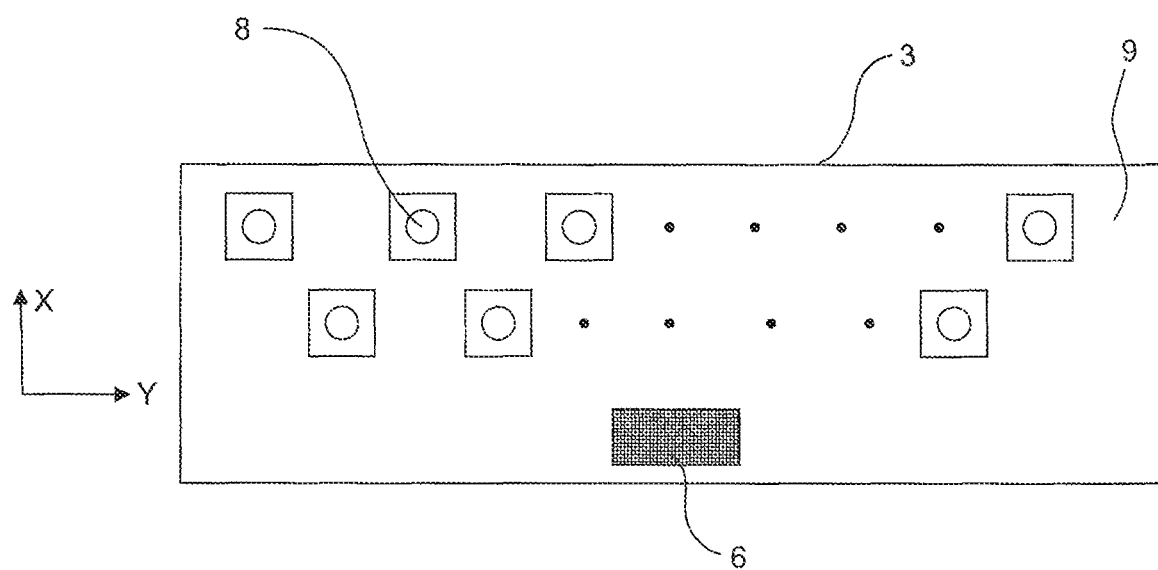
FIG. 3 shows an apparatus for cleaning a fluid according to an embodiment.

The sensor device 6 comprises at least one sensor 10. The electromagnetic radiation 5 detected by the at least one sensor 10 could originate directly from the radiation source device 3 and/or could have been reflected by the photocatalysis device 4 or any other object. According to one embodiment, at least one sensor 10 of the sensor device 6 is arranged on the carrier device 9. FIGS. 2 and 3 show this embodiment. The at least one sensor is accordingly arranged between the radiation sources 8 on the carrier device 9. Such a sensor detects the electromagnetic radiation 5 reflected by the photocatalysis device 4. According to a further embodiment, the at least one sensor 10 of the sensor device 6 is arranged to the side of the radiation source device 3. This at least one sensor 10 is also arranged to the side of the carrier device 9 and to the side of the photocatalysis device 4. Along the height axis Z, this at least one sensor 10 is arranged between the photocatalysis device 4 and the radiation source device 3.

The photocatalysis surface 4a comprises at least one photocatalytic material. The photocatalytic material is a semiconductor, preferably titanium (IV) oxide, $TiO_2$. The photocatalysis surface 4a in this case comprises regions 12 comprising the photocatalytic material. However, other embodiments of the photocatalysis surface 4a are also conceivable. When using titanium dioxide, it is advantageous for the radiation source device 3 to emit electromagnetic radiation 5 having a wavelength of less than 400 nm, preferably in a range of from 380 nm to 315 nm.

An efficiency $\eta_{tot}$ of the apparatus 1 for cleaning a fluid is a product comprising an optical or geometric efficiency $\eta_{opt}$, an efficiency $\eta_{Rs}$ of the radiation source device 3 and an efficiency $\eta_{Pc}$ of the photocatalysis device 4. The radiation parameter is the radiant power of the radiation source device. The sensor device 6 detects a value which changes analogously to the radiation parameter, such that the change in radiation parameter can be determined. The total radiant power $P_{Tot}$ of the radiation source device 3 is the product of the number N of radiation sources and the radiant power $P_N$ of the individual radiation sources 8. The radiation source device 3 can emit electromagnetic radiation 5 with an optimal radiation parameter or optimal radiant power $P_{TotOPT}$. This optimal radiant power $P_{TotOPT}$ can be achieved by a first number $N_1$ of radiation sources 8 which are operated with a maximum operating current $I_{max}$. The provided total number $N_{tot}$ of radiation sources 8 in the radiation source device 3 is greater than the first number $N_1$, however.

Figure 5:
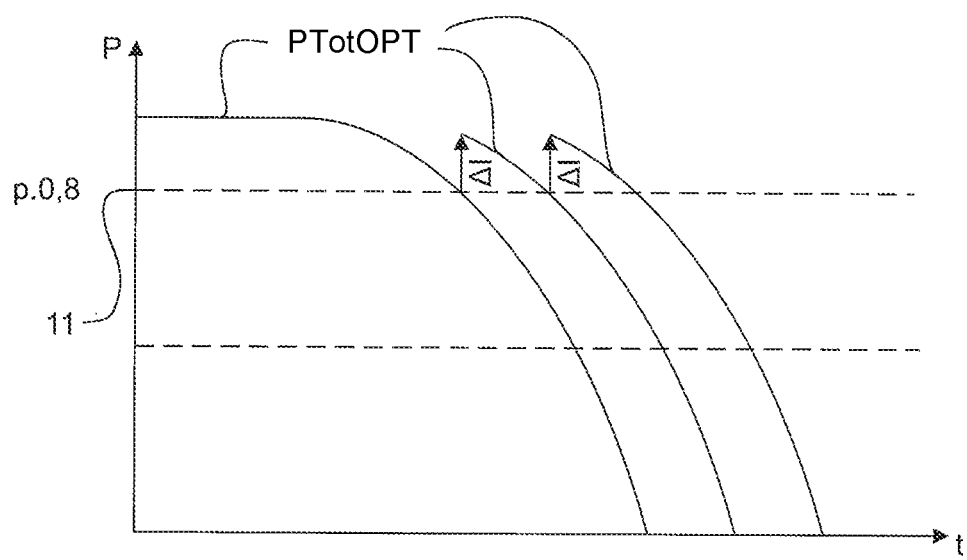
FIG. 5 is a graph of the radiation parameter as a function of the operating time.

According to one embodiment, the at least one control parameter is an operating current $I_O$. The operating current $I_O$ is smaller than the maximum operating current $I_{max}$, at least in a first operating state. The operating number $N_O$ of radiation sources 8 corresponds to the total number $N_{tot}$ of radiation sources 8. A larger number $N_O$ of radiation sources 8 is thus operated with a smaller operating current $I_O$, as a result of which the optimal radiation parameter $P_{totOPT}$ is emitted. In the case of a deviation of the radiation parameter from a setpoint value range in the form of falling below a threshold value 11, the operating current $I_O$ of the operated radiation sources 8 is increased by an amount $\Delta I$ by means of the control device 7. The increase in the operating current $I_O$ is dimensioned such that the optimal radiation parameter, preferably in the form of the optimal total radiant power $P_{TotOPT}$, is emitted by the radiation source device 3 by means of the unchanged operating number $N_O$ of radiation sources 8. This increase can preferably take place even more times in the form of further operating states, a deviation of the radiation parameter from a setpoint value range, in the form of falling below a threshold value 11, being detected in each further operating state. In a final operating state, the operating current $I_O$ is advantageously equal to the maximum operating current $I_{max}$. This embodiment is shown in FIG. 5, which shows the radiation parameter as a function of the operating time. A threshold value was assumed in this case that is 80% of the optimal radiation parameter. A further line is drawn at approx. 50% of the optimal radiation parameter. This would characterise the maximum service life of the radiation source device 3. It can be seen that the maximum service life is significantly increased.

Figure 6:
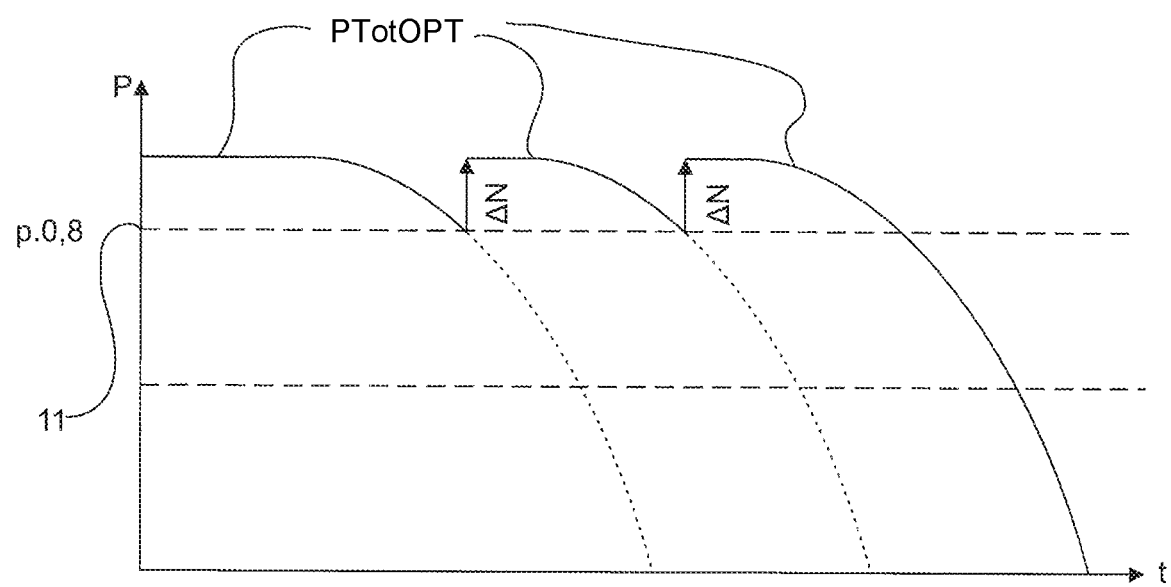
FIG. 6 is a graph of the radiation parameter as a function of the operating time.

According to one embodiment, the at least one control parameter is an operating number $N_O$ of radiation sources 8. At least in a first operating state, the operating number $N_O$ of radiation sources 8 is smaller than the total number $N_{tot}$ of radiation sources 8. The operating number $N_O$ of radiation sources 8 is preferably operated with the maximum operating current $I_{max}$, as a result of which the optimal radiation parameter $P_{totOPT}$ is emitted. The operating number $N_O$ advantageously corresponds to the first number $N_1$. In the case of a deviation of the radiation parameter from a setpoint value range in the form of falling below a threshold value 11, the operating number $N_O$ of radiation sources 8 is increased by an amount $\Delta N$ by means of the control device. The increase in the operating number $N_O$ of radiation sources 8 is dimensioned such that the optimal radiation parameter in the form of the optimal total radiant power $P_{TotOPT}$ is emitted by the radiation source device 3 with the unchanged operating current $I_O$. This increase can preferably take place even more times in the form of further operating states, a deviation of the radiation parameter from a setpoint value range, in the form of falling below a threshold value, being detected in each further operating state. In a final operating state, the operating number $N_O$ of radiation sources is advantageously equal to the total number $N_{tot}$ of radiation sources 8. This embodiment is shown in FIG. 6, which shows the radiation parameter as a function of the operating time. A threshold value was assumed in this case that is 80% of the optimal radiation parameter. A further line is drawn at approx. 50% of the optimal radiation parameter. This would characterise the maximum service life of the radiation source device 3. It can be seen that the maximum service life is significantly increased.

According to a further advantageous embodiment, two control parameters are provided in the form of the operating number $N_O$ of radiation sources 8 and the operating current $I_O$. At least in a first operating state, the operating number $N_O$ of radiation sources is smaller than the total number $N_{tot}$ of radiation sources 8. At least in a first operating state, the operating current $I_O$ is smaller than the maximum operating current $I_{max}$. In this case, it is advantageous that the operating number $N_O$ of radiation sources 8 is increased by the amount $\Delta N$ and the operating current $I_O$ of the operated radiation sources 8 is increased by an amount $\Delta I$ by means of the control device in the case of a deviation of the radiation parameter from a setpoint value range in the form of falling below a threshold value. The increase in the operating number $N_O$ and the operating current $I_O$ of radiation sources 8 is dimensioned such that the optimal radiation parameter, preferably in the form of the optimal total radiant power $P_{TotOPT}$, is emitted by the radiation source device. This increase can take place even more times in the form of further operating states, a deviation of the radiation parameter from a setpoint value range, in the form of falling below a threshold value 11, being detected in each further operating state. In a final operating state, the operating number $N_O$ of radiation sources is advantageously equal to the total number $N_{tot}$ of radiation sources 8, and the operating current $I_O$ is advantageously equal to the maximum operating current $I_{max}$.

Such apparatuses have the advantage that the service life is increased considerably; the user of a corresponding device having the apparatus 1 does not have to bear any maintenance costs, for example for replacing the radiation source device. The present apparatus combines detecting electromagnetic radiation with a smart LED controller.

The applicant reserves the right to claim all the features disclosed in the application documents as essential to the invention, provided that these are novel individually or in combination over the prior art. It is further noted that features which can be advantageous per se have also been described in the individual drawings. A person skilled in the art will immediately recognise that a particular feature described in one drawing can also be advantageous without adopting further features from said drawing. A person skilled in the art will also recognise that advantages can also result from a combination of a plurality of features shown in individual or in different drawings.

LIST OF REFERENCE SIGNS

1 Apparatus for cleaning a fluid
2 Through-channel for the fluid
3 Radiation source device
4 Photocatalysis device
4a Photocatalysis surface
5 Electromagnetic radiation
6 Sensor device
7 Control device
8 Radiation source
9 Carrier device
10 Sensor
11 Setpoint/threshold value or setpoint/threshold value range
12 Region comprising photocatalytic material
X Longitudinal axis
Y Width axis
Z Height axis

What is claimed is:

1. An apparatus for cleaning a fluid, comprising a through-channel for the fluid, a radiation source device, and a photocatalysis device, the radiation source device emitting electromagnetic radiation, it being possible for the photocatalysis device to be exposed to at least some of the electromagnetic radiation in order to generate a photocatalytic reaction,
wherein a sensor device is provided to detect at least one change in radiation parameters of the electromagnetic radiation, a control device being connected to the sensor device via signals, it being possible to modify at least one control parameter of the radiation source device by means of the control device in case of a deviation of the radiation parameter from a setpoint/threshold value or setpoint/threshold range,
wherein the radiation source device comprises a total number ($N_{tot}$) of radiation sources and the at least one control parameter is an operating number ($N_O$) of radiation sources, and
wherein, in a first operating state, the operating number ($N_O$) of radiation sources is smaller than the total number ($N_{tot}$) of radiation sources and the radiation source device is emitting electromagnetic radiation with an optimal radiation parameter, it being possible for the operating number ($N_O$) of radiation sources to be increased by means of the control device in case of a deviation of the radiation parameter from a setpoint value range in a form of falling below a threshold value such that the optimal radiation parameter continues being emitted by the radiation source device with an unchanged operating current ($I_O$).

2. The apparatus according to claim 1, wherein the photocatalysis device comprises a photocatalysis surface which comprises at least one photocatalytic material, the photocatalytic material being a semiconductor; the radiation source device emitting electromagnetic radiation having a wavelength of less than 400 nm, the radiation source device emitting electromagnetic radiation having a wavelength in a range from 380 nm to 315 nm.

3. The apparatus according to claim 1, wherein the radiation sources are light-emitting diodes (LEDs), an efficiency ($\eta$tot) of the apparatus for cleaning a fluid being a product comprising an optical or geometric efficiency ($\eta$opt), an efficiency (IRs) of the radiation source device and an efficiency ($\eta$Pc) of the photocatalysis device, it being possible for electromagnetic radiation having an optimal radiation parameter to be emitted by the radiation source devices, a first number (N1) of radiation sources being operable for emission of the optimal radiation parameter, the first number (N1) of radiation sources being operable with a maximum operating current (Imax).

4. The apparatus according to claim 3, wherein the total number (Ntot) of radiation sources in the radiation source device is greater than or equal to 2, the total number (Ntot) of radiation sources in the radiation source device being greater than the first number (N1).

5. The apparatus according to claim 1, wherein two control parameters are provided in the form of the operating number ($N_O$) of radiation sources and the operating current ($I_O$), the operating number ($N_O$) of radiation sources being smaller than the total number ($N_{tot}$) of radiation sources at least in a first operating state, the operating current ($I_O$) being smaller than a maximum operating current ($I_{max}$) at least in a first operating state, it being possible for the operating number ($N_O$) of radiation sources and the operating current ($I_O$) of the operated radiation sources to be increased by means of the control device in the case of a deviation of the radiation parameter from a setpoint value range in the form of falling below a threshold value.

6. The apparatus according to claim 1, wherein the at least one radiation source is arranged on a carrier device, the carrier device being arranged substantially opposite the photocatalysis device, the through-channel for the fluid being provided between the carrier device and the photocatalysis device.

7. The apparatus according to claim 6, wherein the sensor device comprises at least one sensor, wherein the electromagnetic radiation that is at least one of emitted directly by the radiation source device or reflected by the photocatalysis device is detected by the at least one sensor, the at least one sensor being arranged on the carrier device, and the at least one sensor of the sensor device being arranged to a side of the radiation source device.

8. A method for controlling an apparatus for cleaning a fluid, in particular air, comprising a through-channel for the fluid, a radiation source device and a photocatalysis device, wherein the radiation source device emits electromagnetic radiation, and wherein the photocatalysis device can be exposed to at least some of the electromagnetic radiation in order to generate a photocatalytic reaction, the method comprising:
 a) detecting at least one radiation parameter of the electromagnetic radiation by means of a sensor device;
 b) comparing data detected by the sensor device with a setpoint value range by means of the control device; and
 c) modifying at least one control parameter of the radiation source device,
  wherein the radiation source device comprises a total number ($N_{tot}$) of radiation sources and the at least one control parameter is an operating number ($N_O$) of radiation sources, and
  wherein in a first operating state the operating number ($N_O$) of radiation sources being smaller than the total number ($N_{tot}$) of radiation sources and the radiation source device is emitting electromagnetic radiation with an optimal radiation parameter, it being possible for the operating number ($N_O$) of radiation sources to be increased by means of the control device in case of a deviation of the radiation parameter from a setpoint value range in a form of falling below a threshold value such that the optimal radiation parameter continues being emitted by the radiation source device with an unchanged operating current ($I_O$).

9. The method according to claim 8, wherein two control parameters are provided in the form of the operating number ($N_O$) of radiation sources and the operating current ($I_O$), the operating number ($N_O$) of radiation sources being smaller than the total number ($N_{tot}$) of radiation sources at least in a first operating state, the operating current ($I_O$) being smaller than a maximum operating current ($I_{max}$) at least in a first operating state, the operating number ($N_O$) of radiation sources and the operating current ($I_O$) of the operated radiation sources being increased by means of the control device in the case of a deviation of the radiation parameter from a setpoint value range in the form of falling below a threshold value.

10. A household appliance comprising an apparatus for cleaning a fluid according to claim 1.

11. An air conditioning system comprising an apparatus for cleaning a fluid according to claim 1.

12. Apparatus for cleaning a fluid, comprising a through-channel for the fluid, a radiation source device and a photocatalysis device, the radiation source device emitting electromagnetic radiation, it being possible for the photocatalysis device to be exposed to at least some of the electromagnetic radiation in order to generate a photocatalytic reaction,
 wherein a sensor device is provided to detect at least one change in radiation parameters of the electromagnetic radiation, a control device being connected to the sensor device via signals, it being possible to modify at least one control parameter of the radiation source device by means of the control device in case of a deviation of the radiation parameter from a setpoint/threshold value or setpoint/threshold range,
 wherein an operating number ($N_O$) of radiation sources corresponding to a total number ($N_{tot}$) of radiation sources and the at least one control parameter is an operating current ($I_O$),
 wherein in a first operating state the operating current ($I_O$) being smaller than a maximum operating current ($I_{max}$) and the radiation source device is emitting electromagnetic radiation with an optimal radiation parameter, it being possible for the operating current ($I_O$) of the operated radiation sources to be increased by means of the control device in the case of a deviation of the radiation parameter from a setpoint value range in a form of falling below a threshold value such that such that the optimal radiation parameter continues being emitted by the radiation source device with an unchanged operating number ($N_O$) of radiation sources.

13. A method for controlling an apparatus for cleaning a fluid, comprising a through-channel for the fluid, a radiation source device and a photocatalysis device, wherein the radiation source device emits electromagnetic radiation, wherein the photocatalysis device can be exposed to at least some of the electromagnetic radiation in order to generate a photocatalytic reaction, the method comprising:
 a) detecting at least one radiation parameter of the electromagnetic radiation by means of a sensor device;
 b) comparing data detected by the sensor device with a setpoint value range by means of the control device; and
 c) modifying at least one control parameter of the radiation source device,
  wherein an operating number ($N_O$) of radiation sources corresponding to a total number ($N_{tot}$) of radiation sources and the at least one control parameter is an operating current ($I_O$), and
  wherein in a first operating state the operating current ($I_O$) being smaller than a maximum operating current ($I_{max}$) and the radiation source device is emitting electromagnetic radiation with an optimal radiation parameter,
 it being possible for the operating current ($I_O$) of the operated radiation sources to be increased by means of the control device in case of a deviation of the radiation parameter from a setpoint value range in a form of falling below a threshold value such that such that the optimal radiation parameter continues being emitted by the radiation source device with an unchanged operating number ($N_O$) of radiation sources.

* * * * *